US00RE36260E

United States Patent [19]

Smith et al.

[11] E Patent Number: Re. 36,260

[45] Reissued Date of Patent: Jul. 27, 1999

[54] HAND HOLDABLE HUMAN SKIN TREATMENT APPARATUS

[75] Inventors: Margaret M. Smith, Reno, Nev.; Robson L. Splane, Jr., Granada Hills, Calif.; Sean M. Montgomery, Goleta, Calif.; Ravi K. Sawhney, Canoga Park, Calif.; Robert N. Englin, Newhall, Calif.; William P. Debley, Jr., Winnetka, Calif.

[73] Assignee: MGB Technologies Corp., Sparks, Nev.

[21] Appl. No.: 08/824,951

[22] Filed: Mar. 27, 1997

Related U.S. Patent Documents

Reissue of:

[64] Patent No.: 5,514,167
Issued: May 7, 1996
Appl. No.: 08/327,605
Filed: Oct. 24, 1994

[51] Int. Cl.[6] ..... A61N 1/18

[52] U.S. Cl. ..... 607/75; 607/63; 607/151

[58] Field of Search ..... 607/115, 63, 64, 607/46, 50, 74–76, 145, 146, 149–151

[56] References Cited

U.S. PATENT DOCUMENTS

| | | | |
|---|---|---|---|
| 712,220 | 2/1902 | Vetter | 607/145 |
| 3,107,672 | 10/1963 | Hofman | 607/145 |
| 4,323,073 | 4/1982 | Ferris | 607/46 |
| 4,996,987 | 3/1991 | Petrofsky | 607/46 X |
| 5,012,816 | 5/1991 | Lederer | 607/150 X |
| 5,069,211 | 12/1991 | Bartelt et al. | 607/46 X |

FOREIGN PATENT DOCUMENTS

| | | | |
|---|---|---|---|
| 2751130 | 5/1979 | Germany | 67/151 |
| 9004997 | 5/1990 | WIPO | 607/145 |

*Primary Examiner*—Jeffrey R. Jastrzab
*Attorney, Agent, or Firm*—Jack C. Munro

[57] ABSTRACT

An electrical human skin treatment apparatus which comprises a housing within which is incorporated an electrical circuit. The housing includes a pair of terminals which are spaced apart. The user's hand must be in contact with one terminal with the other terminal to be in contact with the area of application such as the face or neck of the user. The electrical circuit includes a slow voltage current rise to minimize the possibility of electrical shock to the user. A switch is incorporated on the exterior of the housing to not only activate the apparatus, but also to select anaphoresis or cataphoresis.

3 Claims, 2 Drawing Sheets

HAND HOLDABLE HUMAN SKIN TREATMENT APPARATUS

Matter enclosed in heavy brackets [ ] appears in the original patent but forms no part of this reissue specification; matter printed in italics indicates the additions made by reissue.

BACKGROUND OF THE INVENTION

1) Field of the Invention

The field of this invention relates to devices which are for the purpose of rejuvenation of the skin of a human.

2) Description of the Prior Art

It has been found in the past that a human can perform certain procedures on one's skin in order to enhance the skin to make it more healthy so that its general overall appearance is improved. For example, the application of certain cleansing creams and certain softening cremes has been known to enhance the appearance of the skin. It has also been known that applying a small electrical current to one's skin will improve the skin.

In the past, there has been little advancement in recent years of devices which enhance the skin with an electric charge. There has been an endless number of compositions of creams, but in actuality there has been little use of any device to apply an electric charge to one's skin. Previously, the devices which were constructed to imply an electric charge did not take into consideration as to the type of electric charge, it just being an electric charge was used. Additionally, such devices of the prior art have been constructed to be cumbersome and unattractive in appearance. It is well known that in order to entice women to use such an apparatus, with women being the normal user, the apparatus must be attractive in appearance and operate simply as possible.

SUMMARY OF THE INVENTION

The apparatus of the present invention comprises a hand holdable, portable, small in size, electrical charge producing apparatus designed primarily to be of therapeutic value in the treatment of human skin.

The apparatus includes a battery powered circuit contained within a housing. Exteriorly mounted on the housing are a pair of electrical conductors which are spaced apart. One conductor is designed to be in continuous contact with the hand of the user. The remaining electrical conductor is to be applied against the area of the skin that is to be treated. [This remaining] *One of the* electrical [conductor] *conductors* is to be enlarged with generally a horseshoe type shape being preferred. *The remaining electrical conductor is also enlarged in the shape of a straight strip.* The electrical circuit includes a slow current rise so as to minimize the possibility of electrical shock to the user. The housing includes a switch which can be pressed to select between a positive and a negative position. When in the positive position, a positive charge or cataphoresis is transmitted to the user. When in the negative position, a negative charge or anaphoresis is transmitted to the user. The negative position is to be utilized to effect opening of the pores of one's skin. The positive position is to be used at an appropriate time to effect closing of the pores of the skin of the user.

The primary objective of the present invention is to produce a small in size, portable, human skin treatment apparatus which uses a small charge of electrical energy to effect substantially superior treatment of one's skin than was heretofore possible.

Another objective of the present invention is directed to an apparatus which is primarily intended for facial treatment of a human and the apparatus is constructed within an exterior housing which is shaped to facilitate application of the apparatus to the various contours of the face and neck in a highly efficacious manner.

Another objective of the present invention is to provide [is] a compact portable apparatus by which self treatment *is* facilitated.

Another objective of the present invention is to construct a human skin treatment apparatus which can be manufactured relatively inexpensively and therefore sold to the ultimate consumer at a relatively inexpensive price.

Another objective of the present invention is to construct a human skin treatment apparatus which can be operated by even the most unskilled individual.

DETAILED DESCRIPTION OF THE PREFERRED EMBODIMENT

Figure 1:
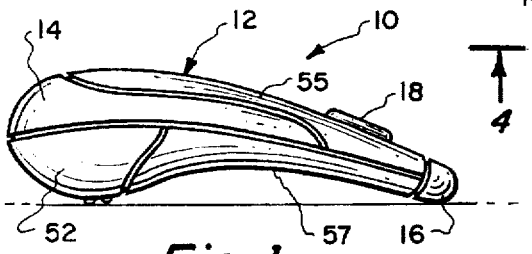
FIG. 1 is a side elevational view of the human skin treatment apparatus of the present invention.
Figure 2:
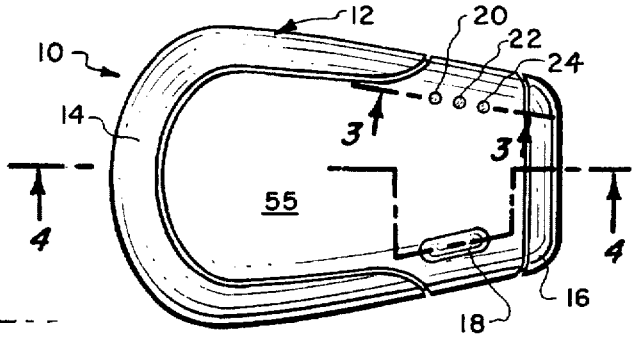
FIG. 2 is a top plan view of the human skin treatment apparatus of the present invention.
Figure 3:
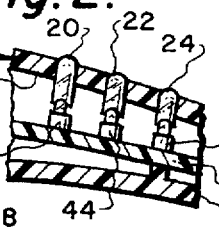
FIG. 3 is a cross-sectional view taken along line 3—3 of FIG. 2 showing more clearly the light emitting diodes that are observable in conjunction with the apparatus.
Figure 4:
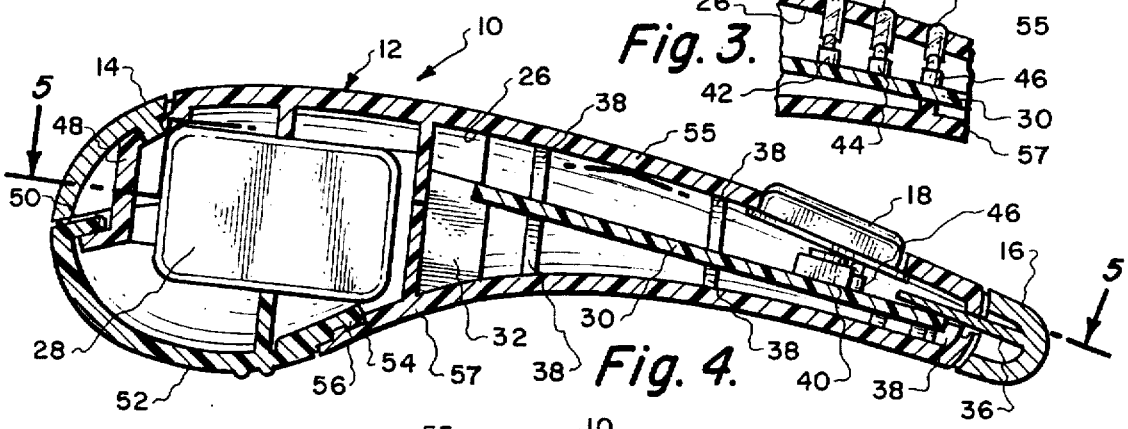
FIG. 4 is a cross-sectional view taken along line 4—4 of FIG. 2 showing in more detail the internal components of the apparatus.
Figure 5:
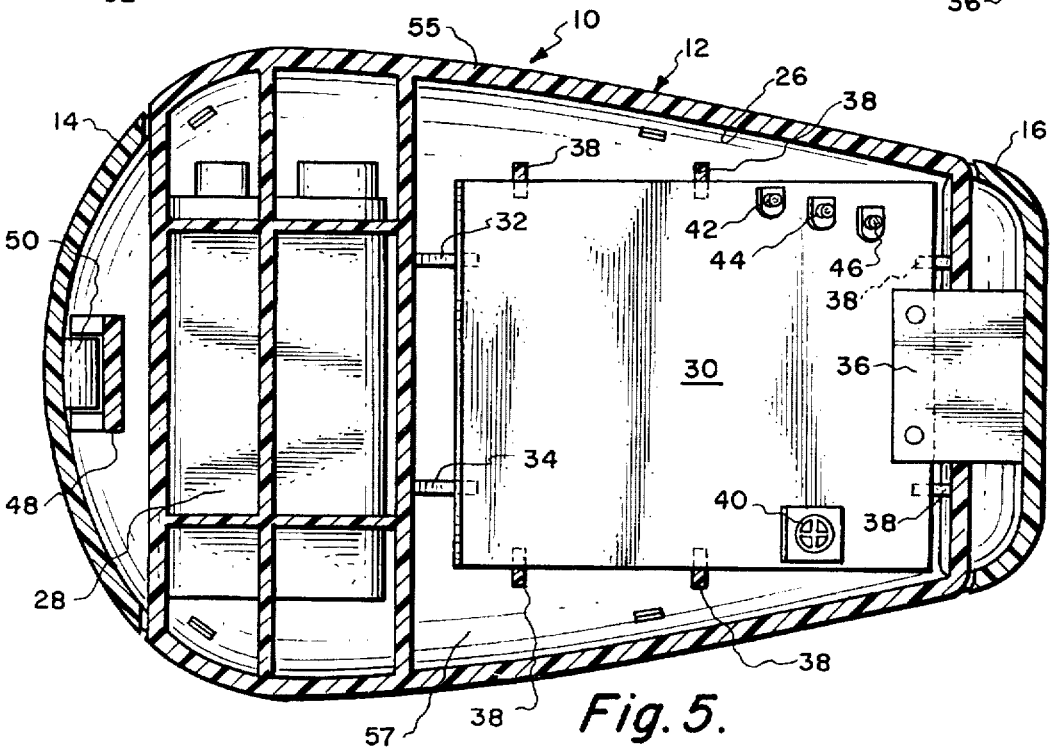
FIG. 5 is a cross-sectional view taken along line 5—5 of FIG. 4, again showing in more detail the internal components of the apparatus.

Referring particularly to the drawings there is shown the apparatus 10 of this invention which is located within housing 12. The housing 12 is basically formed of rigid sheet material, such as a plastic, and has a slightly arcuate configuration when viewed from the side edge as shown in FIG. 1. The front end of the housing 12 is enlarged as opposed to the rear end. Mounted within the front end of the housing 12 is a horseshoe shaped electrical conductor 14. Mounted within the rear end of the housing 12 is a second electrical conductor 16 which is basically in the shape of a straight strip. *It is to be observed from the drawings that conductors 14 and 16 each define an enlarged area of contact as opposed to a point type of contact which is so common in the prior art.*

The housing 12 is actually composed of two separate plastic parts 55 and 57 which are snapped together. On the upper surface of the housing 12 is an on/off button 18 and three in number of light emitting diode lenses 20, 22 and 24. Incorporated within the interior of the housing 12 is an internal compartment 26. Included within the compartment 26 is a battery 28 and printed circuit board 30. The printed circuit board 30 is held in position by rails 32, 34 and 38 which are mounted within internal compartment 26. Electrical connection between the printed circuit board 30 and the electrical conductor 16 is accomplished by plate 36 which is integral with the electrical conductor 16. An appropriate electrical connection (not shown) is to be established between the printed circuit board 30 and the electrical conductor 14.

Included within the circuit board 30 is a switch 40. Also included in the circuit board 30 are three different light-emitting diodes 42, 44 and 46 which are to connect respectively to the light-emitting diode lenses 20, 22 and 24. The electrical conductor 14 is securely mounted on arm 48 which in turn engages with a flange 50 of a battery cover plate 52. This arm 48 securely holds in position conductor 14 on the housing 12. Access into the battery 28 is provided by the battery cover plate 52. Battery cover plate 52 includes at one end a protuberance. 56 that cooperates with a groove 54 formed within the housing 12 and at the other end has a flange 50 that is to be snugly snapped in position in conjunction with arm 48 of the housing 12.

Figures 6, 7:
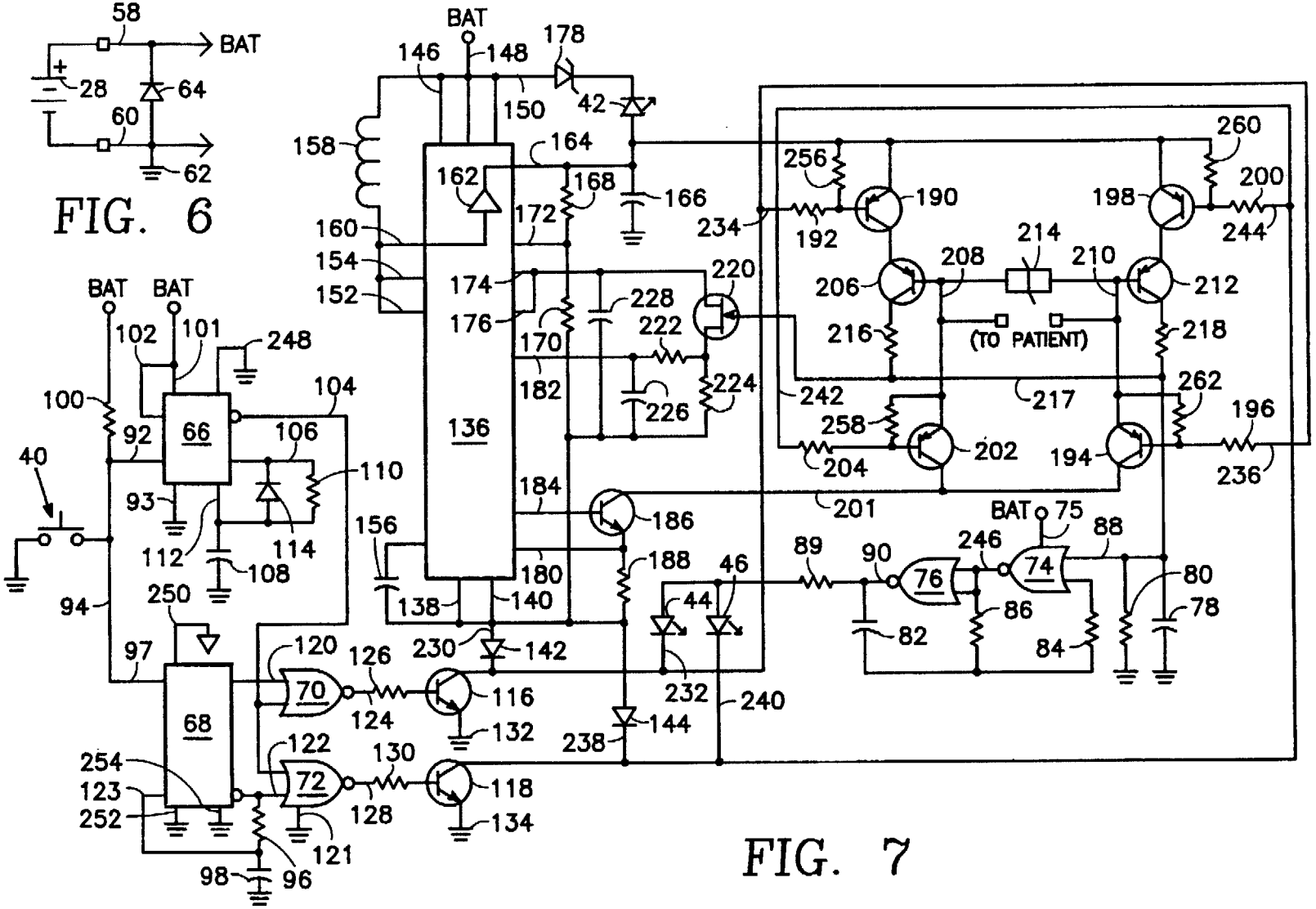
FIG. 6 is an electrical schematic view of the battery circuit utilized in conjunction with the circuit incorporated within the apparatus of the present invention.
FIG. 7 is an overall electrical circuit of the apparatus of the present invention.

Referring particularly to FIG. 6 of the drawing, there is shown the battery circuit for the battery 28. The conductor 58 connects to the positive side of the battery 28 with conductor 60 connecting to the negative side of the battery 28. Conductor 60 is electrically grounded as shown at 62. In between conductor 60 and conductor 58 there is located a diode 64. The diode 64 is for the purpose of protecting the circuitry in case of a temporary incorrect connection when installing of the battery 28. The positive output of conductor 58 is supplied to each component of the circuit in FIG. 7 where indicated by a conducting line and the reference "BAT". The integrated circuits 66, 68, 70, 72, 74 and 76 are all constantly powered by the battery 28, such powering being represented by "BAT" line 75 of integrated circuit 74. These integrated circuits 70, 72, 74 and 76 are also grounded and are represented by ground line 121 of integrated circuit 72. Integrated circuits 66 and 68 could comprise a "Dual D-Flip Flop", part No. TC4013BP, manufactured by Motorola Corporation of Santa Clara, Calif. Integrated circuits 70, 72, 74 and 76 could comprise a "Quad Dual Input Nor Gate", part No. CD4001BP, also manufactured by Motorola Corporation. Care has been taken so that very low amounts of power is consumed when the hand held device of this invention is not in use. Hence there are used large resistances throughout the circuits 66, 68, 70, 72, 74 and 76. The other circuits within the overall circuit of FIG. 7 are not powered constantly but are turned on and made active by activation of switch 40.

Integrated circuits 74 and 76, along with capacitors 78 and 82 and resistors 80, 84 and 86 form an oscillator. This oscillator is used to activate the light-emitting diodes 44 and 46 but never both diodes simultaneously. The lens of diode 44 is to be red in color and denote anaphoresis while the lens of diode 46 is to be green in color to denote cataphoresis. This activation is to be in a flashing manner, that is on and off, which is designed to attract attention of the user to the fact that the hand held device 10 has been activated by switch 40 being pressed. Specifically, as long as input conductor 88 of integrated circuit 74 is held low (that is, ground), then the output conductor 90 of integrated circuit 76 repeatedly charges and discharges capacitor 82. If conductor 88 receives a higher voltage which is greater than one-half of the voltage of the battery, then the oscillating action stops and the output line is held at a high output which is equivalent to the voltage of the battery. This output is conducted through resistor 89 to illuminate constantly either diode 44 or diode 46 but never both simultaneously if the hand held device of this invention has been activated by switch 40.

Turning on of the hand held device 10 is accomplished by the following procedure: If switch 40 is temporarily closed, electrical conductor 92 of integrated circuit 66 immediately goes low and electrical conductor 94 of integrated circuit 68 also goes low. The purpose for resistor 96 and capacitor 98 is to filter noise and also prevent false triggering of integrated circuit 68 which is connected to conductor 122 by conductor 123. Upon release of switch 40, conductors 92 and 94 will incur a rising voltage due to being driven high by resistor 100. Integrated circuits 66 and 68 are a dual-type flip flop triggered by rising voltages on its clock pins that are connected to conductors 92 and 94. So when conductor 92 goes high, the clock pin which connects to conductor 106 becomes the same voltage as the pin of integrated circuit 66 that connects with conductor 102. This voltage is the high battery voltage. This high battery voltage is used to activate integrated circuits 66 and 68 as is represented by line 101 of circuit 66. The pin of the integrated circuit 66 that connects with conductor 104 makes the opposite transition going from battery voltage to ground. After the voltage in conductor 106 goes high, capacitor 108 begins to be charged by resistor 110. Charging capacitor 108 to a higher voltage continues until conductor 112, which connects with integrated circuit 66, reaches one-half of the battery voltage. Then the integrated circuit 66 is reset which means the output from conductor 106 goes low and the voltage from conductor 104 goes high (battery voltage). The time it takes for this cycle of charging capacitor 108 and resetting of the flip flop is normally about two minutes. Diode 114 is used to immediately discharge capacitor 108 when the resetting of integrated circuit 66 occurs.

One of the factors in the design of the hand held apparatus 10 was to provide both anaphoresis and cataphoresis functions through one easy to use human interface. This interface is switch 40. Each time switch 40 is pressed when the hand held device 10 is already activated, the consumer reverses the direction of current flow from anaphoresis to cataphoresis and vice versa. This is accomplished through the integrated circuits 66, 68, 70 and 72.

It is again noted that when the hand held device 10 is turned on, the output from conductor 104 is low (ground). This forces either transistor 116 or 118 to saturate into a conducting state depending upon the conduction of integrated circuit 68. It is to be noted that both transistors 116 and 118 cannot be on simultaneously. This is because the flip flop can never have both conductor 120 and conductor 122 at the same potential at the same time. Whenever a rising voltage occurs in conductor 94, the flip flop outputs of conductors 120 and 122 toggle between the high voltage (battery) and low voltage (ground). Transistor 116 is turned on when integrated circuit 70 within output conductor 124 provides current through resistor 126. Transistor 118 is turned on when the integrated circuit 72 provides current into conductor 128 through resistor 130. The emitter of transistor 116 is connected to ground by conductor 132. The emitter of transistor 118 is similarly connected to ground by conductor 134. When transistor 116 is tuned on, light emitting diode 44 will be flashing from the oscillator mentioned earlier. Likewise whenever transistor 118 is turned on, the light emitting diode 46 will be flashing.

Regardless of which transistor 116 or 118 is on, the pins of integrated circuit 136 will be driven low by conductors 138 and 140. When transistor 116 is turned on, conductors 138 and 140 are driven through diode 142. If transistor 118 is turned on, the conductors 138 and 140 are driven low through diode 144. Since conductors 146, 148 and 150 are constantly connected to the positive battery voltage, the low voltage in conductors 138 and 140 in effect turn on integrated circuit 136. The integrated circuit 136 could comprise a "Universal Switching Regulator Subsystem", part No. VA78540DC, manufactured by National Semiconductor Corporation of Santa Clara, Calif.

The integrated circuit 136 is a monolithic switching voltage regulator. It has an internal oscillator (not shown) which causes internal transistors (not shown) at conductors 152 and 154 to turn on and off. The duly cycle and frequency of these oscillations are determined by the value of capacitor 156 which is connected to integrated circuit 136. Whenever the internal transistors of circuit 136 are on, current flows through inductor 158. Whenever the internal transistors are off, the existing magnetic field in inductor 158 collapses and a momentary voltage rise occurs within conductor 160. This temporary voltage spike causes current to flow in integrated circuit 136 through an internal diode 162 and then through conductor 164 into storage capacitor 166. By a continuation of the oscillation from the internal transistors, the voltage at capacitor 166 rises higher and higher.

The resistors 168 and 170 form a voltage divider and present this reduced voltage, a representation of output voltage within conductor 164, to the integrated circuit 136 through conductor 172. The pin that connects with conductor 172 and the pin that connects with conductor 174 are inputs to an internal voltage comparator (not shown). The output of this comparator controls the amount of the oscillations of the internal transistors previously mentioned. Conductor 174 is connected to a constant reference voltage through conductor 176 of the integrated circuit 136. So, when the pin of the integrated circuit 136 that connects with conductor 172 rises above the voltage within conductor 174, the comparator turns off the transistor oscillations which cause the voltage within conductor 164 to rise. This performs a closed loop feedback mechanism to control the voltage within conductor 164. The voltage within conductor 164 was selected to provide optimum anaphoresis and cataphoresis effect of the hand held device 10.

It was seen as beneficial to provide an indicator for the consumer that would show when the battery was nearing the point of being drained. Diodes 178 and 42 provide a path for current to flow from the output voltage from conductor 164 to the battery. The integrated circuit 136 has the ability to regulate the voltage within conductor 164 over a wide range of battery voltages. Hence when the battery voltage is falling lower and lower, a point is reached where the voltage within conductor 164 overcomes the zener breakdown voltage of diode 178 and current begins to flow through both diodes 178 and 42. The current through light-emitting diode 42 causes it to illuminate giving the consumer an indication of low battery voltage.

The integrated circuit 136 also has an internal operational amplifier (not shown) whose inverting input is connected by conductor 180 and non-inverting input is connected by conductor 182 whose output is within conductor 184. The operational amplifier output is used for activating transistor 186. The current through transistor 186 then flows through resistor 188 to conductor 138 which should be at zero volts. A voltage is formed across resistor 188 and this voltage is fed back through conductor 180 into the operational amplifier of the integrated circuit 136. This operational amplifier of integrated circuit 136, transistor 186 and resistor 188 form a closed loop feedback which controls the current in resistor 188. Furthermore, the current is controlled by the voltage at the other operational amp input which is connected to conductor 182. The voltage at conductor 182 will be discussed later.

Transistors 116 and 118, as mentioned previously, are turned on but not simultaneously when the hand held device 10 turned on. These transistors 116 and 118 subsequently control four other transistors. When transistor 116 is turned on, then transistor 190 is turned on by current through resistor 192. Transistor 194 is turned on by current through resistor 196. Likewise, when transistor 118 is turned on, then transistor 198 is turned on by current through resistor 200 and transistor 202 is turned on by current through resistor 204.

In effect when transistor 116 is turned on, then current flows from integrated circuit 136, through conductor 164, through transistor 190, through the emitter/base of transistor 206, out through conductor 208, through the patient, back into conductor 210, through transistor 194, through conductor 201, through transistor 186 and resistor 188, and back to the integrated circuit 136 by conductor 138. This is the anaphoresis mode. In the cataphoresis mode transistor 118 is activated, then current flows through transistor 198, through emitter/base of transistor 212, out through conductor 210, through the patient, back into conductor 208, through transistor 202, through transistor 186 and resistor 188, and back again to the integrated circuit 136 by way of conductor 138. It is to be noted that the patient (or consumer) receives a controlled voltage from the integrated circuit 136 which is controlled according to the selection of switch 40. A bidirectional diode protection device in the form of transorb 214 is interconnected between conductors 208 and 210 to protect the patient from a higher voltage in case of failure of the hand held device 10.

Resistors 256, 260, 258 and 262 which connect between the emitter and the base of transistors 190, 198, 202 and 194, respectively, are off bias resistors which keep the appropriate transistors turned off during operation of the other transistors. In other words, when transistors 190 and 194 are operated, transistors 198 and 202 are turned off. When transistors 198 and 202 are operated, transistors 190 and 194 are turned off.

Finally, it was deemed unique to be able to provide a slow rise time to the current which the patient receives. To accomplish this the circuit senses the moment of contact with the patient and slowly raises the current from zero to 0.3 milliamps maximum. This is accomplished as follows. When the patient completes a circuit across conductors 208 and 210, then current flows in either the base of transistor 206 or the base of transistor 212 depending upon anaphoresis or cataphoresis. The base current of 206 causes current to flow through resistor 216 into conductor 217. Likewise, the base current of transistor 212 causes current to flow through resistor 218 into conductor 217. The result is that the voltage in conductor 217 rises from ground to a higher voltage. When this voltage rises enough (to at least one-half the voltage of the battery), the aforementioned oscillator slops and either light-emitting diode 44 or light-emitting diode 46 illuminates constantly. Also the transistor 220 is turned on since the gate of the transistor 220 is connected to conductor 217.

When transistor 220 is turned on, the integrated circuit 136 reference voltage at conductor 176 is connected to resistors 222 and 224. This causes current to flow through resistor 222 and slowly charge capacitor 226. This slow voltage rise in the integrated circuit 136 within conductor 182 is reflected by a slow current rise at the patient When the patient disconnects from the circuit, capacitor 226 is discharged through resistors 222 and 224. A capacitor 228 was added in conjunction with conductor 176 to filter noise and provide storage of charge which is needed for the sudden turning on of transistor 220.

The output of integrated circuit 74 is supplied through conductor 246 to comprise a dual input into integrated circuit 76. The unused pins of integrated circuits 66 and 68 are connected directly to ground to avoid misfirings by means of conductors 93, 248, 250, 252 and 254. A pin of integrated circuit 68 is connected by conductor 123 to conductor 122.

What is claimed is:

1. A hand holdable human skin treatment apparatus to be used by a human user comprising:

a housing, said housing having an internal chamber, battery powered electrical circuitry being contained within said internal chamber for generating an operating voltage and current, said housing including an activating switch, said activating switch being connected to said electrical circuitry and being manually operable to activate said electrical circuitry to apply said voltage and current;

said housing including a first electrical conducting terminal and a second electrical conducting terminal, said first electrical conducting terminal and said second electrical conducting terminal being connected to said electrical circuitry, said first electrical conducting being spaced from said second electrical conducting terminal[, said second electrical conducting terminal adapted to be in continuous contact with the user's hand, said first electrical conducting terminal adapted to be placed within contact of the skin of the user that is to be treated]; and said housing being enlarged in the area of said first electrical conducting terminal, said first electrical conducting terminal being horseshoe shaped providing a large surface area [thereby facilitating contact with neck and face areas of the human user].

2. The hand holdable human skin treatment apparatus as defined in claim 1 wherein:

said electrical circuitry including slow voltage current rise means which causes the operating voltage and current within said electrical circuitry to rise slowly so as to minimize the possibility of electrical shock to the human user.

3. The hand holdable human skin treatment apparatus as defined in claim 1 wherein:

said housing including a reversing current switch for reversing said current, said reversing current switch being connected to said electrical circuitry, said reversing current switch being manually movable between a positive position and a negative position, with said reversing current switch in said positive position a cataphoresis charge is conducted between said first electrical conducting terminal and said second electrical conducting terminal, with said reversing current switch in said negative position an anaphoresis charge is conducted between said first electrical conducting terminal and said second electrical conducting terminal.

* * * * *